United States Patent
Lyon et al.

(10) Patent No.: US 9,218,663 B2
(45) Date of Patent: *Dec. 22, 2015

(54) APPARATUS AND METHOD FOR AUTOMATIC IMAGE GUIDED ACCURACY VERIFICATION

(75) Inventors: Torsten M. Lyon, Golden, CO (US); Troy L. Holsing, Nashville, TN (US); Jerome R. Edwards, Nashville, TN (US); Christopher B. Lee, Nashville, TN (US); Evan Austill, Jr., Nashville, TN (US)

(73) Assignee: Veran Medical Technologies, Inc., St. Louis, MO (US)

( * ) Notice: Subject to any disclaimer, the term of this patent is extended or adjusted under 35 U.S.C. 154(b) by 1051 days.

This patent is subject to a terminal disclaimer.

(21) Appl. No.: 13/035,945

(22) Filed: Feb. 26, 2011

(65) Prior Publication Data

US 2011/0184276 A1    Jul. 28, 2011

Related U.S. Application Data

(60) Division of application No. 11/410,143, filed on Apr. 25, 2006, now Pat. No. 7,920,909, which is a continuation-in-part of application No. 11/224,028, filed on Sep. 13, 2005, now abandoned.

(51) Int. Cl.
*A61B 6/00* (2006.01)
*G06T 7/00* (2006.01)
(Continued)

(52) U.S. Cl.
CPC .............. *G06T 7/0028* (2013.01); *G06T 7/0038* (2013.01); *G06T 7/2033* (2013.01); *A61B 5/11* (2013.01); *A61B 6/00* (2013.01); *A61B 6/547* (2013.01); *A61B 2576/00* (2013.01)

(58) Field of Classification Search
CPC ........ A61B 2576/00; A61B 6/00; A61B 5/11; A61B 6/547
USPC .................................................. 600/407–480
See application file for complete search history.

(56) References Cited

U.S. PATENT DOCUMENTS 3,788,324 A    1/1974 Lim
4,421,106 A    12/1983 Uehara
(Continued)

FOREIGN PATENT DOCUMENTS

DE    19751761    10/1998
DE    19725137    1/1999
(Continued)

OTHER PUBLICATIONS

Medical Industry Today [online] "New Navigational Aid Could Improve Hip Replacement Outcomes" Jul. 11, 1997.
(Continued)

*Primary Examiner* — Vani Gupta
(74) *Attorney, Agent, or Firm* — Bryan Cave LLP

(57) ABSTRACT

A method includes receiving during a first time interval associated with a path of motion of a dynamic body, image data associated with a plurality of images of the dynamic body. The plurality of images include an indication of a position of a first marker coupled to a garment at a first location, and a position of a second marker coupled to the garment at a second location. The garment is coupled to the dynamic body. During a second time interval, an image from the plurality of images is automatically identified that includes a position of the first marker that is substantially the same as a position of a first localization element relative to the dynamic body and a position of the second marker that is substantially the same as a position of the second localization element relative to the dynamic body.

12 Claims, 7 Drawing Sheets

(51) Int. Cl.
  *G06T 7/20* (2006.01)
  *A61B 5/11* (2006.01)

(56) References Cited

U.S. PATENT DOCUMENTS

| | | | |
|---|---|---|---|
| 4,583,538 A | 4/1986 | Onik et al. |
| 5,053,042 A | 10/1991 | Bidwell |
| 5,081,997 A | 1/1992 | Bosley et al. |
| 5,158,088 A | 10/1992 | Nelson et al. |
| 5,186,174 A | 2/1993 | Schlondorff et al. |
| 5,238,004 A | 8/1993 | Sahatjian et al. |
| 5,251,165 A | 10/1993 | James, III |
| 5,251,635 A | 10/1993 | Dumoulin et al. |
| 5,265,610 A | 11/1993 | Darrow et al. |
| 5,295,493 A | 3/1994 | Radisch |
| 5,348,011 A | 9/1994 | NessAiver |
| 5,377,678 A | 1/1995 | Dumoulin et al. |
| 5,391,199 A | 2/1995 | Ben-Haim |
| 5,437,292 A | 8/1995 | Kipshidze et al. |
| 5,483,691 A | 1/1996 | Heck et al. |
| 5,483,961 A | 1/1996 | Kelly et al. |
| 5,577,502 A | 11/1996 | Darrow et al. |
| 5,581,183 A | 12/1996 | Lindstedt et al. |
| 5,644,612 A | 7/1997 | Moorman et al. |
| 5,671,739 A | 9/1997 | Darrow et al. |
| 5,718,241 A | 2/1998 | Ben-Haim et al. |
| 5,730,129 A | 3/1998 | Darrow et al. |
| 5,740,808 A | 4/1998 | Panescu et al. |
| 5,765,561 A | 6/1998 | Chen et al. |
| 5,769,789 A | 6/1998 | Wang |
| 5,769,861 A | 6/1998 | Vilsmeier |
| 5,771,306 A | 6/1998 | Stork et al. |
| 5,787,886 A | 8/1998 | Kelly et al. |
| 5,803,089 A | 9/1998 | Ferre et al. |
| 5,814,022 A | 9/1998 | Antanavich et al. |
| 5,814,066 A | 9/1998 | Spotnitz |
| 5,833,608 A | 11/1998 | Acker |
| 5,840,025 A | 11/1998 | Ben-Haim |
| 5,868,673 A | 2/1999 | Vesely |
| 5,928,248 A | 7/1999 | Acker |
| 5,951,461 A | 9/1999 | Nyo |
| 5,978,696 A | 11/1999 | VomLehn et al. |
| 6,016,439 A | 1/2000 | Acker |
| 6,019,724 A | 2/2000 | Gronningsaeter et al. |
| 6,026,173 A | 2/2000 | Svenson et al. |
| 6,078,175 A | 6/2000 | Foo |
| 6,122,538 A | 9/2000 | Sliwa, Jr. et al. |
| 6,122,541 A | 9/2000 | Cosman et al. |
| 6,132,396 A | 10/2000 | Antanavich et al. |
| 6,139,508 A | 10/2000 | Kilcoyne et al. |
| 6,144,875 A | 11/2000 | Schweikard et al. |
| 6,167,296 A | 12/2000 | Shahidi |
| 6,173,201 B1 | 1/2001 | Front |
| 6,188,355 B1 | 2/2001 | Gilboa |
| 6,198,959 B1 | 3/2001 | Wang |
| 6,201,987 B1 | 3/2001 | Dumoulin |
| 6,226,543 B1 | 5/2001 | Gilboa et al. |
| 6,226,548 B1 | 5/2001 | Foley et al. |
| 6,233,476 B1 | 5/2001 | Strommer et al. |
| 6,235,038 B1 | 5/2001 | Hunter et al. |
| 6,236,875 B1 | 5/2001 | Bucholz et al. |
| 6,246,896 B1 | 6/2001 | Dumoulin et al. |
| 6,246,898 B1 | 6/2001 | Vesely et al. |
| 6,253,770 B1 | 7/2001 | Acker et al. |
| 6,254,550 B1 | 7/2001 | McNamara et al. |
| 6,267,769 B1 | 7/2001 | Truwit |
| 6,275,560 B1 | 8/2001 | Blake et al. |
| 6,282,442 B1 | 8/2001 | DeStefano et al. |
| 6,285,902 B1 | 9/2001 | Kienzle, III et al. |
| 6,298,259 B1 | 10/2001 | Kucharczyk et al. |
| 6,314,310 B1 | 11/2001 | Ben-Haim et al. |
| 6,314,311 B1 | 11/2001 | Williams et al. |
| 6,314,312 B1 | 11/2001 | Wessels et al. |
| 6,317,616 B1 | 11/2001 | Glossop |
| 6,317,619 B1 | 11/2001 | Boernert et al. |
| 6,330,356 B1 | 12/2001 | Sundareswaran et al. |
| 6,332,089 B1 | 12/2001 | Acker et al. |
| 6,332,891 B1 | 12/2001 | Himes |
| 6,335,617 B1 | 1/2002 | Osadchy et al. |
| 6,335,623 B1 | 1/2002 | Damadian et al. |
| 6,340,363 B1 | 1/2002 | Bolger et al. |
| 6,347,240 B1 | 2/2002 | Foley et al. |
| 6,348,058 B1 | 2/2002 | Melkent et al. |
| 6,351,573 B1 | 2/2002 | Schneider |
| 6,351,659 B1 | 2/2002 | Vilsmeier |
| 6,361,759 B1 | 3/2002 | Frayne et al. |
| 6,362,821 B1 | 3/2002 | Gibson et al. |
| 6,368,331 B1 | 4/2002 | Front et al. |
| 6,369,571 B1 | 4/2002 | Damadian et al. |
| 6,373,998 B2 | 4/2002 | Thirion et al. |
| 6,379,302 B1 | 4/2002 | Kessman et al. |
| 6,380,732 B1 | 4/2002 | Gilboa |
| 6,381,485 B1 | 4/2002 | Hunter et al. |
| 6,402,762 B2 | 6/2002 | Hunter et al. |
| 6,418,238 B1 | 7/2002 | Shiratani et al. |
| 6,421,551 B1 | 7/2002 | Kuth et al. |
| 6,424,856 B1 | 7/2002 | Vilsmeier et al. |
| 6,425,865 B1 | 7/2002 | Salcudean et al. |
| 6,430,430 B1 | 8/2002 | Gosche |
| 6,434,415 B1 | 8/2002 | Foley et al. |
| 6,434,507 B1 | 8/2002 | Clayton et al. |
| 6,437,571 B1 | 8/2002 | Danby et al. |
| 6,442,417 B1 | 8/2002 | Shahidi et al. |
| 6,445,186 B1 | 9/2002 | Damadian et al. |
| 6,445,943 B1 | 9/2002 | Ferre et al. |
| 6,455,182 B1 | 9/2002 | Silver |
| 6,461,372 B1 | 10/2002 | Jensen et al. |
| 6,468,265 B1 | 10/2002 | Evans et al. |
| 6,469,508 B1 | 10/2002 | Damadian et al. |
| 6,470,066 B2 | 10/2002 | Takagi et al. |
| 6,470,207 B1 | 10/2002 | Simon et al. |
| 6,473,635 B1 | 10/2002 | Rashe |
| 6,477,400 B1 | 11/2002 | Barrick |
| 6,478,793 B1 | 11/2002 | Cosman et al. |
| 6,478,802 B2 | 11/2002 | Kienzle, III et al. |
| 6,483,948 B1 | 11/2002 | Spink et al. |
| 6,484,049 B1 | 11/2002 | Seeley et al. |
| 6,485,413 B1 | 11/2002 | Boppart et al. |
| D466,609 S | 12/2002 | Glossop |
| D466,610 S | 12/2002 | Ashton et al. |
| 6,490,467 B1 | 12/2002 | Bucholz et al. |
| 6,490,475 B1 | 12/2002 | Seeley et al. |
| 6,490,477 B1 | 12/2002 | Zylka et al. |
| 6,491,699 B1 | 12/2002 | Henderson et al. |
| 6,491,702 B2 | 12/2002 | Heilbrun et al. |
| 6,493,574 B1 | 12/2002 | Ehnholm et al. |
| 6,496,007 B1 | 12/2002 | Damadian et al. |
| 6,501,981 B1 | 12/2002 | Schweikard et al. |
| 6,504,893 B1 | 1/2003 | Flohr et al. |
| 6,504,894 B2 | 1/2003 | Pan et al. |
| 6,516,213 B1 | 2/2003 | Nevo |
| 6,517,485 B2 | 2/2003 | Torp et al. |
| 6,527,443 B1 | 3/2003 | Vilsmeier et al. |
| 6,535,756 B1 | 3/2003 | Simon et al. |
| 6,538,634 B1 | 3/2003 | Chui et al. |
| 6,539,127 B1 | 3/2003 | Roche et al. |
| 6,541,973 B1 | 4/2003 | Danby et al. |
| 6,544,041 B1 | 4/2003 | Damadian |
| 6,547,782 B1 | 4/2003 | Taylor |
| 6,558,333 B2 | 5/2003 | Gilboa et al. |
| 6,562,059 B2 | 5/2003 | Edwards et al. |
| 6,567,687 B2 | 5/2003 | Front et al. |
| 6,574,498 B1 | 6/2003 | Gilboa |
| 6,580,938 B1 | 6/2003 | Acker |
| 6,584,174 B2 | 6/2003 | Schubert et al. |
| 6,584,339 B2 | 6/2003 | Galloway, Jr. et al. |
| 6,591,130 B2 | 7/2003 | Shahidi |
| 6,593,884 B1 | 7/2003 | Gilboa |
| 6,606,513 B2 | 8/2003 | Lardo et al. |
| 6,609,022 B2 | 8/2003 | Vilsmeier et al. |
| 6,615,155 B2 | 9/2003 | Gilboa |
| 6,636,757 B1 | 10/2003 | Jascob et al. |
| 6,650,924 B2 | 11/2003 | Kuth et al. |
| 6,666,579 B2 | 12/2003 | Jensen |

(56) References Cited

U.S. PATENT DOCUMENTS

| | | |
|---|---|---|
| 6,674,833 B2 | 1/2004 | Shahidi et al. |
| 6,675,032 B2 | 1/2004 | Chen et al. |
| 6,675,033 B1 | 1/2004 | Lardo et al. |
| 6,687,531 B1 | 2/2004 | Ferre et al. |
| 6,690,960 B2 | 2/2004 | Chen et al. |
| 6,694,167 B1 | 2/2004 | Ferre et al. |
| 6,697,664 B2 | 2/2004 | Kienzle, III et al. |
| 6,702,780 B1 | 3/2004 | Gilboa |
| 6,711,429 B1 | 3/2004 | Gilboa et al. |
| 6,714,629 B2 | 3/2004 | Vilsmeier |
| 6,714,810 B2 | 3/2004 | Grzeszczuk et al. |
| 6,725,080 B2 | 4/2004 | Melkent et al. |
| 6,738,656 B1 | 5/2004 | Ferre et al. |
| 6,772,002 B2 | 8/2004 | Schmidt et al. |
| 6,774,624 B2 | 8/2004 | Anderson et al. |
| 6,782,287 B2 | 8/2004 | Grzeszczuk et al. |
| 6,796,988 B2 | 9/2004 | Melkent et al. |
| 6,799,569 B2 | 10/2004 | Danielsson et al. |
| 6,823,207 B1 | 11/2004 | Jensen et al. |
| 6,826,423 B1 | 11/2004 | Hardy et al. |
| 6,833,814 B2 | 12/2004 | Gilboa |
| 6,850,794 B2 | 2/2005 | Shahidi |
| 6,856,826 B2 | 2/2005 | Seeley et al. |
| 6,856,827 B2 | 2/2005 | Seeley et al. |
| 6,892,090 B2 | 5/2005 | Verard et al. |
| 6,898,303 B2 | 5/2005 | Armato, III et al. |
| 6,899,672 B2 | 5/2005 | Chin et al. |
| 6,907,281 B2 | 6/2005 | Grzeszczuk |
| 6,920,347 B2 | 7/2005 | Simon et al. |
| 6,925,200 B2 | 8/2005 | Wood et al. |
| 6,934,575 B2 | 8/2005 | Ferre et al. |
| 6,947,788 B2 | 9/2005 | Gilboa |
| 6,968,224 B2 | 11/2005 | Kessman et al. |
| 6,978,166 B2 | 12/2005 | Foley et al. |
| 6,992,477 B2 | 1/2006 | Govari |
| 6,996,430 B1 | 2/2006 | Gilboa |
| 7,015,859 B2 | 3/2006 | Anderson |
| 7,015,907 B2 | 3/2006 | Tek et al. |
| 7,035,683 B2 | 4/2006 | Guendel |
| 7,050,845 B2 | 5/2006 | Vilsmeier |
| 7,115,100 B2 | 10/2006 | McRury et al. |
| 7,130,700 B2 | 10/2006 | Gardeski et al. |
| 7,139,601 B2 | 11/2006 | Bucholz et al. |
| 7,153,297 B2 | 12/2006 | Peterson |
| 7,171,257 B2 | 1/2007 | Thomson |
| 7,174,201 B2 | 2/2007 | Govari et al. |
| 7,233,820 B2 | 6/2007 | Gilboa |
| 7,260,426 B2 | 8/2007 | Schweikard et al. |
| 7,300,428 B2 | 11/2007 | Ingenito |
| 7,339,587 B2 | 3/2008 | Kropfeld |
| 7,357,807 B2 | 4/2008 | Donohoe et al. |
| 7,366,562 B2 | 4/2008 | Dukesherer et al. |
| 7,371,067 B2 | 5/2008 | Anderson |
| 7,398,116 B2 | 7/2008 | Edwards |
| 7,481,805 B2 | 1/2009 | Magnusson |
| 7,505,806 B2 | 3/2009 | Masutani et al. |
| 7,555,330 B2 | 6/2009 | Gilboa |
| 7,594,925 B2 | 9/2009 | Danek |
| 7,599,730 B2 | 10/2009 | Hunter et al. |
| 7,641,609 B2 | 1/2010 | Ohnishi |
| 7,659,912 B2 | 2/2010 | Akimoto |
| 7,697,972 B2 | 4/2010 | Verard et al. |
| 7,756,563 B2 | 7/2010 | Higgins |
| 7,889,905 B2 | 2/2011 | Higgins |
| 7,901,348 B2 | 3/2011 | Soper |
| 7,920,909 B2 * | 4/2011 | Lyon et al. ............ 600/407 |
| 7,962,193 B2 * | 6/2011 | Edwards et al. ........ 600/407 |
| 7,969,143 B2 | 6/2011 | Gilboa |
| 7,985,187 B2 | 7/2011 | Wibowo |
| 7,998,062 B2 | 8/2011 | Gilboa |
| 8,016,749 B2 | 9/2011 | Clerc |
| 8,046,052 B2 | 10/2011 | Verard et al. |
| 8,049,777 B2 | 11/2011 | Akimoto |
| 8,064,669 B2 | 11/2011 | Higgins |
| 8,096,957 B2 | 1/2012 | Conquergood et al. |
| 8,102,416 B2 | 1/2012 | Ito |
| 8,150,138 B2 | 4/2012 | Ohnishi |
| 8,150,495 B2 | 4/2012 | Edwards et al. |
| 8,202,213 B2 | 6/2012 | Ito |
| 8,214,015 B2 | 7/2012 | Macaulay et al. |
| 8,218,846 B2 | 7/2012 | Trumer |
| 8,218,847 B2 | 7/2012 | Averbuch |
| 8,219,179 B2 | 7/2012 | Ganatra |
| 8,317,149 B2 | 11/2012 | Greenburg |
| 8,317,726 B2 | 11/2012 | Timberlake et al. |
| 8,382,662 B2 | 2/2013 | Soper |
| 8,428,328 B2 | 4/2013 | Averbuch |
| 8,468,003 B2 | 6/2013 | Gibbs |
| 8,473,032 B2 | 6/2013 | Averbuch |
| 8,483,801 B2 | 7/2013 | Edwards |
| 8,494,246 B2 | 7/2013 | Trumer |
| 8,494,612 B2 | 7/2013 | Vetter |
| 8,611,983 B2 | 12/2013 | Glossop |
| 8,611,984 B2 | 12/2013 | Greenburg |
| 8,632,461 B2 | 1/2014 | Glossop |
| 8,672,836 B2 | 3/2014 | Higgins |
| 8,675,935 B2 | 3/2014 | Higgins |
| 8,696,548 B2 | 4/2014 | Gilboa |
| 8,696,685 B2 | 4/2014 | Gilboa |
| 8,700,132 B2 | 4/2014 | Ganatra |
| 2001/0007918 A1 | 7/2001 | Vilsmeier et al. |
| 2001/0025142 A1 | 9/2001 | Wessels et al. |
| 2001/0029333 A1 | 10/2001 | Shahidi |
| 2001/0031919 A1 | 10/2001 | Strommer et al. |
| 2001/0031985 A1 | 10/2001 | Gilboa et al. |
| 2001/0036245 A1 | 11/2001 | Kienzle et al. |
| 2001/0041835 A1 | 11/2001 | Front et al. |
| 2002/0044631 A1 | 4/2002 | Graumann et al. |
| 2002/0049375 A1 | 4/2002 | Strommer et al. |
| 2002/0049378 A1 | 4/2002 | Grzeszczuk et al. |
| 2002/0070970 A1 | 6/2002 | Wood et al. |
| 2002/0075994 A1 | 6/2002 | Shahidi et al. |
| 2002/0077543 A1 | 6/2002 | Grzeszczuk et al. |
| 2002/0077544 A1 | 6/2002 | Shahidi |
| 2002/0082492 A1 | 6/2002 | Grzeszczuk |
| 2002/0085681 A1 | 7/2002 | Jensen |
| 2002/0115931 A1* | 8/2002 | Strauss et al. ............ 600/420 |
| 2002/0143317 A1 | 10/2002 | Glossop |
| 2002/0161295 A1 | 10/2002 | Edwards et al. |
| 2003/0000535 A1 | 1/2003 | Galloway, Jr. et al. |
| 2003/0004411 A1 | 1/2003 | Govari et al. |
| 2003/0016852 A1 | 1/2003 | Kaufman et al. |
| 2003/0018251 A1 | 1/2003 | Solomon |
| 2003/0023161 A1 | 1/2003 | Govari et al. |
| 2003/0028091 A1 | 2/2003 | Simon et al. |
| 2003/0029464 A1 | 2/2003 | Chen et al. |
| 2003/0032878 A1 | 2/2003 | Shahidi |
| 2003/0040667 A1 | 2/2003 | Feussner et al. |
| 2003/0051733 A1 | 3/2003 | Kotmel et al. |
| 2003/0074011 A1 | 4/2003 | Gilboa et al. |
| 2003/0088179 A1 | 5/2003 | Seeley et al. |
| 2003/0125622 A1 | 7/2003 | Schweikard et al. |
| 2003/0130576 A1 | 7/2003 | Seeley et al. |
| 2003/0139663 A1 | 7/2003 | Graumann |
| 2003/0199785 A1 | 10/2003 | Hibner et al. |
| 2003/0208116 A1 | 11/2003 | Liang et al. |
| 2003/0208122 A1 | 11/2003 | Melkent et al. |
| 2003/0216631 A1 | 11/2003 | Bloch et al. |
| 2003/0220557 A1 | 11/2003 | Cleary et al. |
| 2004/0006268 A1 | 1/2004 | Gilboa et al. |
| 2004/0034300 A1 | 2/2004 | Verard et al. |
| 2004/0049121 A1 | 3/2004 | Yaron |
| 2004/0076259 A1 | 4/2004 | Jensen et al. |
| 2004/0091143 A1 | 5/2004 | Hu |
| 2004/0092815 A1 | 5/2004 | Schweikard et al. |
| 2004/0097805 A1 | 5/2004 | Verard et al. |
| 2004/0097806 A1 | 5/2004 | Hunter et al. |
| 2004/0116803 A1 | 6/2004 | Jascob et al. |
| 2004/0122311 A1 | 6/2004 | Cosman |
| 2004/0138548 A1 | 7/2004 | Strommer et al. |
| 2004/0152970 A1 | 8/2004 | Hunter et al. |
| 2004/0152974 A1 | 8/2004 | Solomon |
| 2004/0167393 A1 | 8/2004 | Solar et al. |
| 2004/0193042 A1 | 9/2004 | Scampini et al. |

(56) References Cited

U.S. PATENT DOCUMENTS

| | | |
|---|---|---|
| 2004/0210125 A1 | 10/2004 | Chen et al. |
| 2004/0249267 A1 | 12/2004 | Gilboa |
| 2005/0010099 A1 | 1/2005 | Raabe et al. |
| 2005/0020900 A1 | 1/2005 | Yngvesson |
| 2005/0027186 A1 | 2/2005 | Chen et al. |
| 2005/0033149 A1 | 2/2005 | Strommer et al. |
| 2005/0038337 A1 | 2/2005 | Edwards |
| 2005/0065433 A1 | 3/2005 | Anderson |
| 2005/0085718 A1 | 4/2005 | Shahidi |
| 2005/0085793 A1 | 4/2005 | Glossop |
| 2005/0107679 A1 | 5/2005 | Geiger et al. |
| 2005/0107688 A1 | 5/2005 | Strommer |
| 2005/0113809 A1 | 5/2005 | Melkent et al. |
| 2005/0137661 A1 | 6/2005 | Sra |
| 2005/0143651 A1 | 6/2005 | Verard et al. |
| 2005/0169510 A1 | 8/2005 | Zuhars et al. |
| 2005/0182295 A1 | 8/2005 | Soper et al. |
| 2005/0182319 A1 | 8/2005 | Glossop |
| 2005/0187482 A1 | 8/2005 | O'Brien et al. |
| 2005/0197568 A1 | 9/2005 | Vass et al. |
| 2005/0203383 A1 | 9/2005 | Moctezuma de la Barrera et al. |
| 2005/0234335 A1 | 10/2005 | Simon et al. |
| 2005/0288574 A1 | 12/2005 | Thornton et al. |
| 2005/0288578 A1 | 12/2005 | Durlak |
| 2006/0004281 A1* | 1/2006 | Saracen ................ 600/414 |
| 2006/0025677 A1 | 2/2006 | Verard et al. |
| 2006/0045318 A1 | 3/2006 | Schoisswohl et al. |
| 2006/0050942 A1 | 3/2006 | Bertram et al. |
| 2006/0050988 A1 | 3/2006 | Kraus et al. |
| 2006/0058647 A1 | 3/2006 | Strommer et al. |
| 2006/0063998 A1 | 3/2006 | von Jako et al. |
| 2006/0064006 A1 | 3/2006 | Strommer et al. |
| 2006/0074292 A1 | 4/2006 | Thomson et al. |
| 2006/0074299 A1 | 4/2006 | Sayeh |
| 2006/0074304 A1 | 4/2006 | Sayeh |
| 2006/0079759 A1 | 4/2006 | Vaillant et al. |
| 2006/0084867 A1 | 4/2006 | Tremblay et al. |
| 2006/0093089 A1 | 5/2006 | Vertatschitsch et al. |
| 2006/0094958 A1 | 5/2006 | Marquart et al. |
| 2006/0106292 A1 | 5/2006 | Anderson |
| 2006/0116634 A1 | 6/2006 | Shachar |
| 2006/0122497 A1 | 6/2006 | Glossop |
| 2006/0142798 A1 | 6/2006 | Holman et al. |
| 2006/0173269 A1 | 8/2006 | Glossop |
| 2006/0173291 A1 | 8/2006 | Glossop |
| 2006/0184016 A1 | 8/2006 | Glossop |
| 2006/0189867 A1 | 8/2006 | Revie et al. |
| 2006/0247511 A1 | 11/2006 | Anderson |
| 2006/0258933 A1 | 11/2006 | Ellis |
| 2006/0270976 A1 | 11/2006 | Savage et al. |
| 2007/0032723 A1 | 2/2007 | Glossop |
| 2007/0038058 A1 | 2/2007 | West et al. |
| 2007/0066887 A1 | 3/2007 | Mire et al. |
| 2007/0110289 A1 | 5/2007 | Fu et al. |
| 2007/0129629 A1 | 6/2007 | Beauregard et al. |
| 2007/0167714 A1 | 7/2007 | Kiraly et al. |
| 2007/0167744 A1 | 7/2007 | Beauregard et al. |
| 2007/0225559 A1 | 9/2007 | Clerc et al. |
| 2007/0232896 A1 | 10/2007 | Gilboa |
| 2007/0244355 A1 | 10/2007 | Shaw |
| 2007/0249896 A1 | 10/2007 | Goldfarb et al. |
| 2007/0276180 A1 | 11/2007 | Greenburg |
| 2008/0071142 A1 | 3/2008 | Gattani et al. |
| 2008/0071143 A1 | 3/2008 | Gattani et al. |
| 2008/0118135 A1 | 5/2008 | Averbuch |
| 2008/0125760 A1 | 5/2008 | Gilboa |
| 2008/0132757 A1 | 6/2008 | Tgavalekos |
| 2008/0140114 A1 | 6/2008 | Edwards et al. |
| 2008/0167639 A1 | 7/2008 | Gilboa |
| 2008/0221442 A1 | 9/2008 | Tolkowsky et al. |
| 2008/0247622 A1 | 10/2008 | Aylward et al. |
| 2008/0255416 A1 | 10/2008 | Gilboa |
| 2008/0262297 A1 | 10/2008 | Gilboa |
| 2008/0262342 A1 | 10/2008 | Averbuch |
| 2008/0269561 A1 | 10/2008 | Banik et al. |
| 2008/0287803 A1 | 11/2008 | Li et al. |
| 2009/0054908 A1 | 2/2009 | Zand et al. |
| 2009/0088600 A1 | 4/2009 | Meloul |
| 2009/0156895 A1 | 6/2009 | Higgins et al. |
| 2009/0156951 A1 | 6/2009 | Averbuch |
| 2009/0209817 A1 | 8/2009 | Averbuch |
| 2009/0227861 A1 | 9/2009 | Ganatra et al. |
| 2009/0240140 A1 | 9/2009 | Fitelzon |
| 2009/0240198 A1 | 9/2009 | Averbuch |
| 2009/0284255 A1 | 11/2009 | Zur |
| 2010/0036241 A1 | 2/2010 | Mayse et al. |
| 2010/0041949 A1 | 2/2010 | Tolkowsky |
| 2010/0160733 A1 | 6/2010 | Gilboa |
| 2012/0046521 A1 | 2/2012 | Hunter et al. |
| 2012/0059220 A1 | 3/2012 | Holsing et al. |
| 2012/0059248 A1 | 3/2012 | Holsing et al. |
| 2012/0065481 A1 | 3/2012 | Hunter et al. |
| 2012/0071753 A1 | 3/2012 | Hunter et al. |
| 2012/0123296 A1 | 5/2012 | Hashimshony et al. |

FOREIGN PATENT DOCUMENTS

| | | |
|---|---|---|
| DE | 19725137 C | 7/1999 |
| DE | 19829224 | 1/2000 |
| DE | 19829224 B | 1/2000 |
| DE | 19909816 | 5/2000 |
| DE | 19909816 A1 | 5/2000 |
| DE | 199909816 | 5/2000 |
| DE | 10000937 | 8/2001 |
| DE | 10000937 B | 8/2001 |
| DE | 10136709 | 2/2003 |
| DE | 10136709 B | 2/2003 |
| DE | 10161160 | 6/2003 |
| DE | 10161160 A1 | 6/2003 |
| DE | 102005010010 | 9/2005 |
| DE | 102005010010 A1 | 9/2005 |
| DE | 102004030836 | 1/2006 |
| DE | 102004030836 A1 | 1/2006 |
| DE | 102005026251 | 1/2006 |
| DE | 102005038394 | 3/2006 |
| DE | 102005038394 A1 | 3/2006 |
| DE | 102005050286 | 4/2006 |
| DE | 1020050505286 A1 | 4/2006 |
| DE | 102004058122 | 7/2006 |
| DE | 102004058122 A1 | 7/2006 |
| EP | 0 501 993 B1 | 9/1992 |
| EP | 0501993 | 9/1992 |
| EP | 0501993 B1 | 9/1992 |
| EP | 0 869 745 B8 | 10/1998 |
| EP | 0869745 | 10/1998 |
| EP | 9 00 048 B1 | 3/1999 |
| EP | 900048 | 3/1999 |
| EP | 0928600 | 7/1999 |
| EP | 9 77 510 A1 | 2/2000 |
| EP | 977510 | 2/2000 |
| EP | 1 079 240 A2 | 2/2001 |
| EP | 1079240 | 2/2001 |
| EP | 1 152 706 B1 | 11/2001 |
| EP | 1152706 | 11/2001 |
| EP | 1 181 897 A2 | 2/2002 |
| EP | 1181897 | 2/2002 |
| EP | 1 319 368 A2 | 6/2003 |
| EP | 1319368 | 6/2003 |
| EP | 1 374 792 A1 | 1/2004 |
| EP | 1 374 793 A1 | 1/2004 |
| EP | 1374792 | 1/2004 |
| EP | 1374793 | 1/2004 |
| EP | 1 391 181 A1 | 2/2004 |
| EP | 1391181 | 2/2004 |
| EP | 1 421 913 A1 | 5/2004 |
| EP | 1421913 | 5/2004 |
| EP | 1 464 285 B1 | 10/2004 |
| EP | 1464285 | 10/2004 |
| EP | 1 504 713 A1 | 2/2005 |
| EP | 1 504 726 A1 | 2/2005 |
| EP | 1504713 | 2/2005 |
| EP | 1504726 | 2/2005 |
| EP | 1 519 140 A1 | 3/2005 |
| EP | 1519140 | 3/2005 |

(56) References Cited

FOREIGN PATENT DOCUMENTS

| | | |
|---|---|---|
| EP | 1 523 951 A2 | 4/2005 |
| EP | 1523951 | 4/2005 |
| EP | 1 561 423 A1 | 8/2005 |
| EP | 1561423 | 8/2005 |
| EP | 1 629 774 A1 | 3/2006 |
| EP | 1 629 789 A1 | 3/2006 |
| EP | 1629774 | 3/2006 |
| EP | 1629789 | 3/2006 |
| EP | 2380550 | 10/2011 |
| FR | 2 876 273 A1 | 4/2006 |
| FR | 2876273 | 4/2006 |
| JP | 2000023941 | 1/2000 |
| WO | 9424933 | 11/1994 |
| WO | 95/01757 A1 | 1/1995 |
| WO | 9501757 | 1/1995 |
| WO | 96/08209 A2 | 3/1996 |
| WO | 96/08209 A3 | 3/1996 |
| WO | 9608209 | 3/1996 |
| WO | 9608209 A2 | 3/1996 |
| WO | 96/10949 A1 | 4/1996 |
| WO | 9610949 | 4/1996 |
| WO | 9626672 | 9/1996 |
| WO | 97/29699 A1 | 8/1997 |
| WO | 97/29709 A1 | 8/1997 |
| WO | 9729699 | 8/1997 |
| WO | 9729709 | 8/1997 |
| WO | 98/36684 A1 | 8/1998 |
| WO | 9836684 | 8/1998 |
| WO | 99/16352 A1 | 4/1999 |
| WO | 9916352 | 4/1999 |
| WO | 9927839 | 6/1999 |
| WO | 99/43253 A1 | 9/1999 |
| WO | 9943253 | 9/1999 |
| WO | 00/16684 A1 | 3/2000 |
| WO | 0016684 | 3/2000 |
| WO | 00/28911 A1 | 5/2000 |
| WO | 0028911 | 5/2000 |
| WO | 00/47103 A2 | 8/2000 |
| WO | 00/49958 A1 | 8/2000 |
| WO | 0047103 | 8/2000 |
| WO | 0049958 | 8/2000 |
| WO | 00/57767 A2 | 10/2000 |
| WO | 0057767 | 10/2000 |
| WO | 00/69335 A1 | 11/2000 |
| WO | 0069335 | 11/2000 |
| WO | 01/01845 A2 | 1/2001 |
| WO | 0101845 | 1/2001 |
| WO | 01/37748 A2 | 5/2001 |
| WO | 0137748 | 5/2001 |
| WO | 01/62134 A2 | 8/2001 |
| WO | 0162134 | 8/2001 |
| WO | 01/64124 A1 | 9/2001 |
| WO | 01/76496 A1 | 10/2001 |
| WO | 01/76497 A1 | 10/2001 |
| WO | 0176496 | 10/2001 |
| WO | 0176497 | 10/2001 |
| WO | 01/87136 A2 | 11/2001 |
| WO | 0187136 | 11/2001 |
| WO | 01/93745 A2 | 12/2001 |
| WO | 0193745 | 12/2001 |
| WO | 02/00093 A2 | 1/2002 |
| WO | 02/00103 A2 | 1/2002 |
| WO | 0200093 | 1/2002 |
| WO | 0200103 | 1/2002 |
| WO | 02/19936 A2 | 3/2002 |
| WO | 02/22015 A2 | 3/2002 |
| WO | 02/24051 A2 | 3/2002 |
| WO | 0219936 | 3/2002 |
| WO | 0222015 | 3/2002 |
| WO | 0224051 | 3/2002 |
| WO | 02/056770 A1 | 7/2002 |
| WO | 02056770 | 7/2002 |
| WO | 02/064011 A2 | 8/2002 |
| WO | 02064011 | 8/2002 |
| WO | 02/082375 A2 | 10/2002 |
| WO | 02082375 | 10/2002 |
| WO | 02/098273 A2 | 12/2002 |
| WO | 02098273 | 12/2002 |
| WO | 2004/046754 A2 | 6/2004 |
| WO | 2004046754 | 6/2004 |
| WO | 2004/060157 A1 | 7/2004 |
| WO | 2004/062497 A1 | 7/2004 |
| WO | 2004060157 | 7/2004 |
| WO | 2004062497 | 7/2004 |
| WO | 2005016166 | 2/2005 |
| WO | 2005/070318 A1 | 8/2005 |
| WO | 2005/077293 A2 | 8/2005 |
| WO | 2005070318 | 8/2005 |
| WO | 2005/101277 A2 | 10/2005 |
| WO | 2005077293 | 10/2005 |
| WO | 2005101277 | 10/2005 |
| WO | 2005/111942 A1 | 11/2005 |
| WO | 2005111942 | 11/2005 |
| WO | 2006/002396 A2 | 1/2006 |
| WO | 2006/005021 A2 | 1/2006 |
| WO | 2006002396 | 1/2006 |
| WO | 2006005021 | 1/2006 |
| WO | 2006/027781 A2 | 3/2006 |
| WO | 2006027781 | 3/2006 |
| WO | 2006/039009 A2 | 4/2006 |
| WO | 2006039009 | 4/2006 |
| WO | 2006/051523 A2 | 5/2006 |
| WO | 2006051523 | 5/2006 |
| WO | 2006/090141 A1 | 8/2006 |
| WO | 2006090141 | 8/2006 |
| WO | 2007/002079 A2 | 1/2007 |
| WO | 2007002079 | 1/2007 |
| WO | 2007/031314 A2 | 3/2007 |
| WO | 2007031314 | 3/2007 |
| WO | 2007033206 | 3/2007 |
| WO | 2007/062051 A2 | 5/2007 |
| WO | 2007062051 | 5/2007 |
| WO | 2007/084893 A2 | 7/2007 |
| WO | 2007084893 | 7/2007 |
| WO | 2007/033206 A2 | 8/2007 |
| WO | 2009159578 | 12/2009 |
| WO | 2012024686 | 2/2012 |

OTHER PUBLICATIONS

Patent Cooperation Treat, International Search Report and Written Opinion from PCT/US06/35548, mailed Aug. 20, 2007, 7 pages Aug. 20, 2007.
European Patent Office, Extended Search Report issued for EP 11818898.6, mailed Dec. 20, 2013, 6 pages Dec. 20, 2013.
Patent Cooperation Treaty, International Search Report issued for PCT/US2011/048669, mailed Apr. 9, 2012, 7 pages Apr. 9, 2012.
Medical Industry Today, "New navigational aid could improve hip replacement outcomes," Jul. 11, 1997.
Educational Highlights from Data Presented at the 5th Joint Meeting of the European Association for Cardio-Thoracic Surgery (EACTS) and the European Society of Thoracic Surgeons (ESTS) "Evidence for Fleece-Bound Sealants in Cardiothoracic Surgery" Sep. 9-13, 2006, 4 pages.
Moore, E. et al. "Needle Aspiration Lung Biopsy: Reevaluation of the Blood Patch Technique in an Equine Model", Radiology, vol. 196, No. 1, Jul. 1995, pp. 183-186.
FDA Approves Lung Sealant, May 31, 2000 [online] [Retrieved on Oct. 17, 2008] Retrieved from the Internet <URL:http://www.meds.com/archive/mol-cancer/2000/05/msg01329.html.

* cited by examiner

US 9,218,663 B2

APPARATUS AND METHOD FOR AUTOMATIC IMAGE GUIDED ACCURACY VERIFICATION

CROSS-REFERENCE TO RELATED APPLICATIONS

This application is a continuation-in-part of U.S. patent application Ser. No. 11/224,028, filed Sep. 13, 2005, now abandoned, entitled "Apparatus and Method for Image Guided Accuracy Verification," the disclosure of which is hereby incorporated by reference in its entirety.

BACKGROUND

The invention relates generally to a medical device and particularly to an apparatus and method associated with image guided medical procedures.

Image guided surgery (IGS), also known as image guided intervention (IGI), enhances a physician's ability to locate instruments within anatomy during a medical procedure. IGS can include 2-dimensional (2-D) and 3-dimensional (3-D) applications.

Existing imaging modalities can capture the movement of dynamic anatomy. Such modalities include electrocardiogram (ECG)-gated or respiratory-gated magnetic resonance imaging (MRI) devices, ECG-gated or respiratory-gated computer tomography (CT) devices, and cinematography (CINE) fluoroscopy. The dynamic imaging modalities can capture the movement of anatomy over a periodic cycle of that movement by sampling the anatomy at several instants during its characteristic movement and then creating a set of image frames or volumes. Such images can be used to help a physician navigate a medical instrument to the desired location on the anatomical body during a medical procedure performed on the anatomical body at a later time.

Typical image-guided medical systems require manual user input to identify a pre-procedural image that corresponds to the same position and orientation of an anatomical body during a medical procedure. These manual operations can lead to greater errors and reduced efficiency in image-guided procedures.

Thus, a need exists for a method and apparatus that can automatically identify pre-procedural images of a targeted anatomical body that can be used to help a physician navigate a medical instrument to a selected location on the anatomical body during a range of motion of the anatomical body.

SUMMARY OF THE INVENTION

Apparatuses and methods for performing gated instrument navigation on dynamic anatomy with automatic image registration are disclosed herein. In one embodiment, a method includes receiving during a first time interval image data associated with a plurality of images of a dynamic body. The plurality of images includes an indication of a position of a first marker on a garment coupled to the dynamic body and a position of a second marker on the garment coupled to the dynamic body. The first marker is coupled to the garment at a first location, and the second marker is coupled to the garment at a second location. The first time interval is associated with a path of motion of the dynamic body. During a second time interval after the first time interval, data is received that is associated with a position of a first localization element relative to the dynamic body, and data is received that is associated with a position of a second localization element relative to the dynamic body. The first localization element is coupled to the garment at the first location, and the second localization element is coupled to the garment at the second location. The second time interval is associated with a path of motion of the dynamic body. During the second time interval, an image from the plurality of images is automatically identified that includes a position of the first marker that is substantially the same as the position of the first localization element relative to the dynamic body and a position of the second marker that is substantially the same as the position of the second localization element relative to the dynamic body.

BRIEF DESCRIPTION OF THE DRAWINGS

The present invention is described with reference to the accompanying drawings.

DETAILED DESCRIPTION

Figure 1:
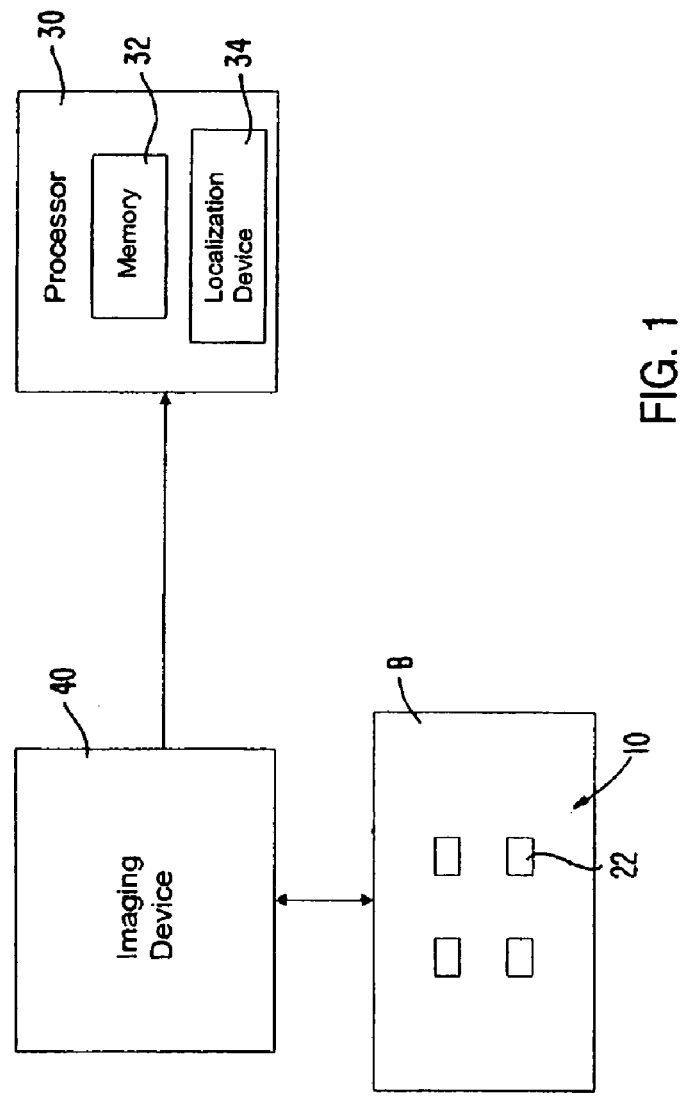
FIG. 1 is a schematic illustration of various devices used with a method according to an embodiment of the invention.

A method according to an embodiment of the invention includes capturing images of a dynamic body during a path of motion of the dynamic body pre-procedurally (also referred to herein as "first time interval"). The images can be used to assist a physician in navigating a medical instrument to a desired location on the dynamic body during a medical procedure performed at a later time (also referred to herein as "second time interval"). The method uses a system configured to automatically perform segmentation, correlation and registration between data obtained in "model space" or "image space" (position data taken pre-procedurally) and data obtained in "physical space" (position data obtained during a later medical procedure).

Specifically, an apparatus is configured to be coupled to a selected dynamic body, such as selected dynamic anatomy of a patient. Dynamic anatomy can be, for example, any portion of the body associated with anatomy that moves during its normal function (e.g., the heart, lungs, kidneys, liver and vasculature). The apparatus can include, for example, two or more markers configured to be coupled to a patient and two or more localization elements configured to be coupled to the patient proximate the markers. In other embodiments, the apparatus can include, for example, a garment configured to be coupled to a patient, two or more markers coupled to the garment, and two or more localization elements coupled to the garment at a location proximate the markers.

A processor, such as a computer, is configured to receive the pre-procedural image data associated with the dynamic body taken during a pre-surgical or pre-procedural first time interval. The image data can include an indication of a position of each of the markers for multiple instants in time during the first time interval. The processor can also receive position data associated with the localization elements during a second time interval in which a surgical procedure or other medical procedure is being performed. The processor can use the position data received from the localization elements and the position data received from the images to automatically identify an image from the pre-procedural images where the position of the markers at a given instant in time during the pre-procedural imaging is substantially the same as the position of the localization elements corresponding to those markers, at a given instant of time during the later medical procedure.

A physician or other healthcare professional can use the images that were automatically identified by the processor during a medical procedure performed during the second time interval, such as, for example, an image-guided medical procedure involving temporal registration and gated navigation. For example, when a medical procedure is performed on a targeted anatomy of a patient, such as a heart, the physician may not be able to utilize an imaging device during the medical procedure to guide him to the targeted area within the patient. Markers or fiducials can be positioned or coupled to the patient proximate the targeted anatomy prior to the medical procedure, and pre-procedural images can be taken of the targeted area during a first time interval. The markers or fiducials can be viewed within the image data, which can include an indication of the position of the markers during a given path of motion of the targeted anatomy (e.g., the heart) during the first time interval. Such motion can be due, for example, to inspiration (i.e., inhaling) and expiration (i.e., exhaling) of the patient, or due to the heart beating. During a medical procedure, performed during a second time interval, such as a procedure on a heart, with the markers coupled to the patient at the same location/position as during the first time interval, the processor receives data from the localization elements associated with a position of the localization elements at a given instant in time during the medical procedure (or second time interval).

Because the markers are positioned at the same location on the patient relative to the dynamic body during both the first time interval and the second time interval, and the localization elements are coupled to the patient proximate the location of the markers, a correlation can be made between the position data in image space and the position data in physical space. For example, a position of the markers at an instant in time during the pre-procedural imaging corresponds to a specific position and orientation of the dynamic body at an instant in time during the path of motion of the dynamic body as viewed in the image data. When the medical procedure is performed during the second time interval, a position of the localization elements likewise corresponds to a specific positioning of the dynamic body at an instant in time during the path of motion of the dynamic body. Although the marker-localization element combinations can move relative to each other, for example, as the dynamic anatomy moves, the markers are in a fixed position relative to the patient during both the first time interval and the second time interval. As stated above, the localization elements are coupled to the patient proximate the markers, thus, when the position of the localization elements (identified during the medical procedure) is substantially the same as the position of the markers (identified in the image space), the image corresponding to that position of the markers is representative of the position of the dynamic body for that instant during the medical procedure.

An automatic segmentation-correlation-registration process can be performed after the image dataset is imported into the processor and the localization elements are connected to the processor. Once performed, the correlation does not change during the course of the procedure and the model space marker positions provide a baseline position for the temporal registration. After the segmentation-correlation and baseline registration has been computed, the localization element locations are sampled automatically and continuously to determine when the dynamic body is at or near the position at which the images were acquired. The affine rigid-body transformation is computed automatically and continuously until a temporal gating threshold is exceeded, indicating that the dynamic body is no longer near the same configuration as where the images were acquired. The automatic process produces simulated real-time, intra-procedural images illustrating the orientation and shape of the targeted anatomy as a catheter or similar structure is navigated to the targeted anatomy. Thus, during the medical procedure, the physician can view selected image(s) of the targeted anatomy that correspond to and simulate real-time movement of the anatomy.

In addition, during a medical procedure being performed during the second time interval, such as navigating an instrument, such as a catheter or needle to a targeted anatomy, the location(s) of an electromagnetic coil coupled to the instrumentation during the second time interval can be superimposed on an image of the instrumentation. The superimposed image(s) of the instrument can then be superimposed on the selected image(s) from the first time interval, providing simulated real time imaging of the instrument location relative to the targeted anatomy. This process and other related methods are described in U.S. Pat. No. 7,398,116, entitled Methods, Apparatuses, and Systems Useful in Conducting Image Guided Interventions, filed Aug. 26, 2003.

Having described above various general principles, several example embodiments of these concepts are now described. These embodiments are only examples, and many other embodiments are contemplated by the principles of the invention, and will be apparent to the artisan in view of the general principles described above and the exemplary embodiments. For example, other possible embodiments can be used to perform some or all of the functions described herein, such as those systems and methods described in U.S. patent application Ser. No. 11/224,028, filed Sep. 13, 2005, now abandoned, entitled "Apparatus and Method for Image Guided Accuracy Verification" (referred to herein as "the '028 application"), the disclosure of which is hereby incorporated by reference in its entirety.

Figure 2:
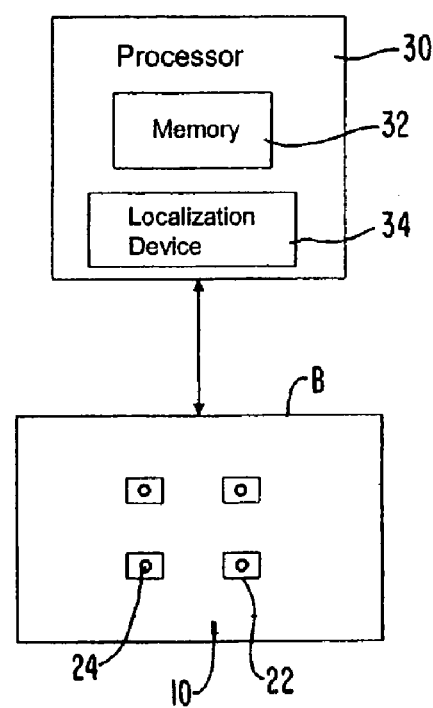
FIG. 2 is a schematic illustration of various devices used with a method according to an embodiment of the invention.

FIGS. 1 and 2 are schematic illustrations of devices that can be used to perform various procedures described herein. An apparatus 10 includes two or more markers or fiducials 22 coupled to a dynamic body B at selected locations, as shown in FIG. 1. The dynamic body B can be, for example, a selected dynamic portion of the anatomy of a patient. The markers 22 are constructed of a material that can be viewed on an image, such as an X-ray. The markers 22 can be, for example, radiopaque, and can be coupled to the dynamic body B using known methods of coupling such devices to a patient, such as with adhesive, straps, etc. FIGS. 1 and 2 illustrate the apparatus 10 having four markers 22, but any number of two or more markers can be used.

An imaging device 40 can be used to take images of the dynamic body B while the markers 22 are coupled to the dynamic body B, pre-procedurally during a first time interval. As stated above, the markers 22 are visible on the images and can provide an indication of a position of each of the markers 22 during the first time interval. The position of the markers 22 at given instants in time through a path of motion of the dynamic body B can be illustrated with the images. The imaging device 40 can be, for example, a computed tomography (CT) device (e.g., respiratory-gated CT device, ECG-gated CT device), a magnetic resonance imaging (MRI) device (e.g., respiratory-gated MRI device, ECG-gated MRI device), an X-ray device, or any other suitable medical imaging device. In one embodiment, the imaging device 40 is a computed tomography—positron emission tomography device that produces a fused computed tomography—positron emission tomography image dataset. The imaging device 40 can be in communication with a processor 30 and send, transfer, copy and/or provide image data taken during the first time interval associated with the dynamic body B to the processor 30.

The processor 30 includes a processor-readable medium storing code representing instructions to cause the processor 30 to perform a process. The processor 30 can be, for example, a commercially available personal computer, or a less complex computing or processing device that is dedicated to performing one or more specific tasks. For example, the processor 30 can be a terminal dedicated to providing an interactive graphical user interface (GUI). The processor 30, according to one or more embodiments of the invention, can be a commercially available microprocessor. Alternatively, the processor 30 can be an application-specific integrated circuit (ASIC) or a combination of ASICs, which are designed to achieve one or more specific functions, or enable one or more specific devices or applications. In yet another embodiment, the processor 30 can be an analog or digital circuit, or a combination of multiple circuits.

The processor 30 can include a memory component 32. The memory component 32 can include one or more types of memory. For example, the memory component 32 can include a read only memory (ROM) component and a random access memory (RAM) component. The memory component can also include other types of memory that are suitable for storing data in a form retrievable by the processor 30. For example, electronically programmable read only memory (EPROM), erasable electronically programmable read only memory (EEPROM), flash memory, as well as other suitable forms of memory can be included within the memory component. The processor 30 can also include a variety of other components, such as for example, co-processors, graphic processors, etc., depending upon the desired functionality of the code.

The processor 30 can store data in the memory component 32 or retrieve data previously stored in the memory component 32. The components of the processor 30 can communicate with devices external to the processor 30 by way of an input/output (I/O) component (not shown). According to one or more embodiments of the invention, the I/O component can include a variety of suitable communication interfaces. For example, the I/O component can include, for example, wired connections, such as standard serial ports, parallel ports, universal serial bus (USB) ports, S-video ports, local area network (LAN) ports, small computer system interface (SCSI) ports, and so forth. Additionally, the I/O component can include, for example, wireless connections, such as infrared ports, optical ports, Bluetooth® wireless ports, wireless LAN ports, or the like.

The processor 30 can be connected to a network, which may be any form of interconnecting network including an intranet, such as a local or wide area network, or an extranet, such as the World Wide Web or the Internet. The network can be physically implemented on a wireless or wired network, on leased or dedicated lines, including a virtual private network (VPN).

As stated above, the processor 30 can receive image data (also referred to herein as "image dataset") from the imaging device 40. The processor 30 can identify the position of selected markers 22 within the image data or voxel space using various segmentation techniques, such as Hounsfield unit thresholding, convolution, connected component, or other combinatory image processing and segmentation techniques. The processor 30 can determine a distance and direction between the position of any two markers 22 during multiple instants in time during the first time interval, and store the image data, as well as the position and distance data, within the memory component 32. Multiple images can be produced providing a visual image at multiple instants in time through the path of motion of the dynamic body. The processor 30 can also include a receiving device or localization device 34, which is described in more detail below.

As shown in FIG. 2, during a second time interval, two or more localization elements 24 are coupled to the markers 22 for use during a medical procedure to be performed during the second time interval. The localization elements 24 are coupled to the patient adjacent the markers 22. The localization elements 24 can be, for example, electromagnetic coils, infrared light emitting diodes, and/or optical passive reflective markers. The markers 22 can include plastic or non-ferrous fixtures or dovetails or other suitable connectors used to couple the localization elements 24 to the markers 22. A medical procedure can then be performed with the markers 22 coupled to the dynamic body B at the same location as during the first time interval when the pre-procedural images were taken. During the medical procedure, the localization elements 24 are in communication or coupled to the localization device 34 included within processor 30. The localization device 34 can be, for example, an analog to digital converter that measures voltages induced onto localization coils in the field; creates a digital voltage reading; and maps that voltage reading to a metric positional measurement based on a characterized volume of voltages to millimeters from a fixed field emitter. Position data associated with the localization elements 24 can be transmitted or sent to the localization device 34 continuously during the medical procedure during the second time interval. Thus, the position of the localization elements 24 can be captured at given instants in time during the second time interval.

The image dataset, the position data for the markers from the first time interval ("model space") and the position data for the localization elements during the second time interval ("physical space") can be used to perform an automatic segmentation, correlation and registration between the data in the model space and the data in the physical space. The result of the analysis is to provide a physician with images that represent the position of a dynamic body during the second time interval when the physician is performing a medical procedure on the dynamic body. The processor 30 can be configured to perform the automatic segmentation-correlation-registration process as described in more detail below.

Figure 8:
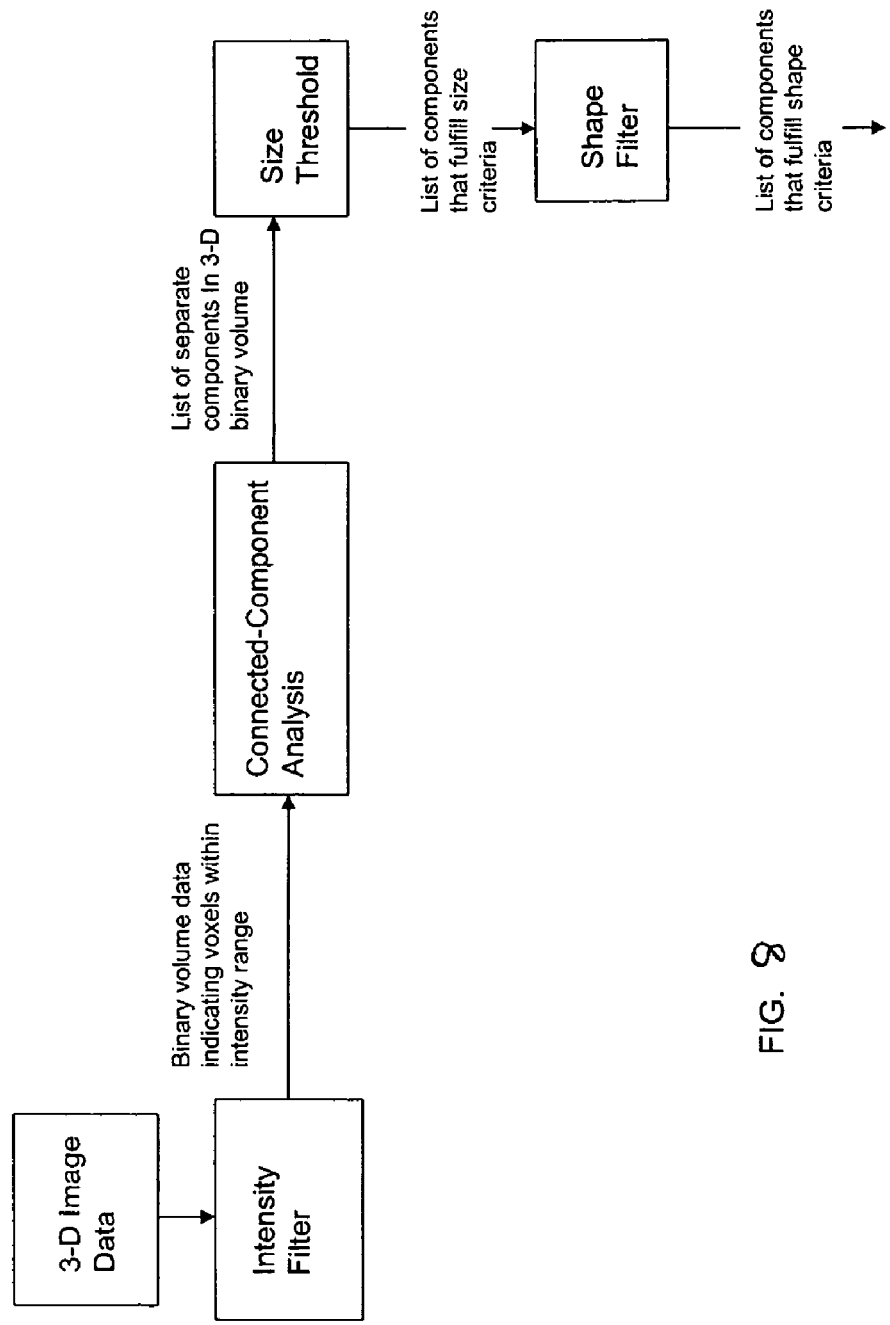
FIG. 8 is a schematic illustration of the flow of information during an automatic segmentation process.

To identify actual position data associated with the markers 22 within the image dataset, the processor 30 can perform an automated segmentation procedure. Segmentation is the process of identifying reference points in the 3-D image dataset. The purpose of the segmentation is to automatically locate potential "landmarks" in the dataset that indicate a location where a marker 22 may be located. Segmentation can be performed in a variety of different manners. For example, a segmentation process can include, intensity filtering, connectivity analysis, and size and shape filtering to identify candidate sensor (e.g., marker) locations, or model space (also referred to herein as "image space") coordinates of the marker 20 candidates. In some example embodiments, the intensity filtering applies domain knowledge to threshold the 3-D image dataset to select only those image values that fall within a designated intensity range that contains the reference points. For example, reference markers can be designated to appear in CT scans with Hounsfield units higher than the anatomical structures within the 3-D image. An example output from an intensity filtering process can include a 3-D binary volume with non-zero entries indicating voxels (i.e., a 3-D data point) with an intensity that falls within the range of values that characterize an image marker, as illustrated in FIG. 8. FIG. 8 is a schematic illustration of the flow of information during one example of an automatic segmentation process.

Figure 5:
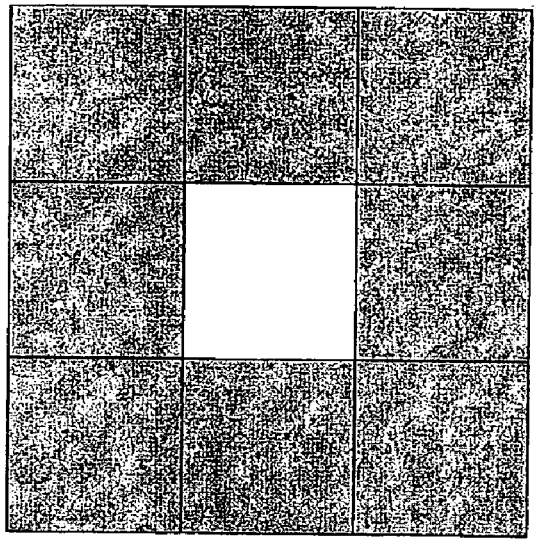
FIG. 5 is a schematic illustration of an example of voxels of a connected-component in a 3-D volume according to an embodiment of the invention.
Figure 6:
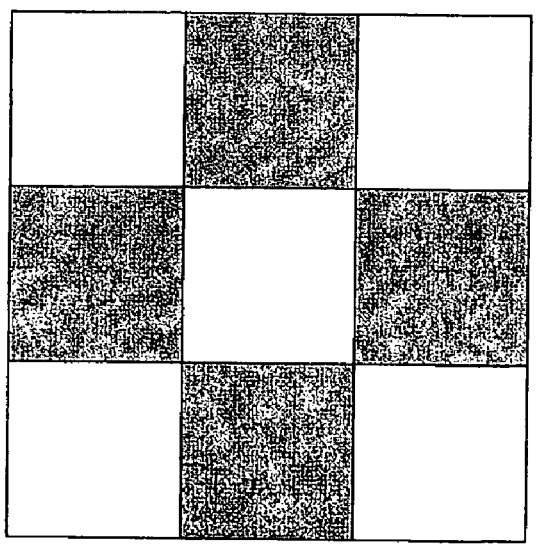
FIG. 6 is a schematic illustration of an example of voxels of a connected-component in a 3-D volume according to an alternative embodiment of the invention.

After filtering the image values based on intensity, a connectivity analysis can be performed. A connectivity analysis can use the output from the intensity filtering to analyze the potential candidates identified in the 3-D image dataset to identify, for example, "connected-components." A connected-component, as used here, is a continuous 3-D region in the 3-D volume (i.e., image dataset) that is connected via adjacent voxels that are in contact with one another. Examples of voxels of connected-components are illustrated in FIGS. 5 and 6. FIG. 5 illustrates a connected-component having 8 connected voxel elements (indicated by the shaded boxes), and FIG. 6 illustrates a connected component having 4 connected voxel elements (indicated by the shaded boxes). From the identified connected-components, information about the connected regions, such as the location of each voxel element, the geometric center, and the volume and bounding perimeter dimensions can be identified. An example output of a connectivity analysis can include, for example, a list of each separate connected-component in the 3-D binary volume, and can be used in the next step in the segmentation process.

Next, in some embodiments, the output from the connectivity analysis, which includes the identified connected-components, can be filtered based on size and shape criteria during a size threshold analysis. First, knowledge about the size of the reference markers can be used to identify and discard any connected-components that are too small or too large to be valid markers. A list of connected-components that fulfill the size criteria can then be evaluated based on the shape of the components during a shape-filtering analysis. Knowledge about the shape of the reference markers can be used to discard any components that do not match the known shape of the reference markers. For example, if the markers are known to be cylindrical, then the connected component shape can be analyzed to determine if the ratio between the major axis and the minor axis is within a set criteria. The output from this step in this example process includes, for example, a list of connected-components that fulfill the shape criteria. Other analysis can be performed depending on the particular marker configuration, such as, for example, checking whether the connected-component shape is symmetric about a centroid of the connected-component.

After the segmentation process is performed, an automatic correlation process can be performed. Correlation as used here is the process of correctly matching reference points between the image or model space and the physical space. Correctly matching the reference points aids in accurately computing the registration between the data in the image space and the data in the physical space without user interaction. The correlation process determines where each of the localization elements is positioned in the model images. Correct correlation is required to compute an affine transform between model space and physical space. The apparatuses and methods described herein enable the process to be automated with minimal user intervention. Automatic correlation results in an understanding of the location of the markers in image space and physical space, as well as the corresponding labeling/identification of each marker in each space.

Because there are a large number of possible solutions, computations of all possible combinations can result in long computation times. According to an embodiment of the invention, the processor 30 can be configured to compute the correlation between the image space and the physical space at a much faster rate (e.g., 2 seconds on a 1.5 GHz G4 Macintosh computer).

Because the number of localization element positions in the physical space is typically smaller than the number of identified marker positions in the model space, a guess at a correlation can be made for three localization element points in physical space. An affine transform registration is then computed between the selected positions of the localization elements 24 in physical space and the model space. The computed registration is then used to transform the remaining localization element positions to model space and determine if any markers exist at the projected locations. A brute force iteration is made in groups of 3 as just described. When projecting the remaining points from physical space to model space to test the correlation guess, a test can be performed for the existence of a marker in model space within a settable threshold 3-D distance. If present, a 3-D error can be computed and the correlation resulting in the lowest error can be noted and recorded. This technique discards points in model space that do not have a corresponding point in physical space (i.e., false positives in the list of marker positions determined during segmentation).

Because the number of localization element positions is relatively low, it can be fairly computationally inexpensive to perform the iterative process described above to search all possible correlation combinations. The process is implemented such that the affine transform used to compute rigid body registration between the model space and the physical space for each 3-point correlation is abstract, and the actual implementation can be defined and determined at runtime. It is possible to improve the speed of the process by stopping the solution search iterations if a solution is identified that meets the specified criteria. For example, when computing the error for a correlation guess, the projection loop-and-fail for the correlation guess can be reduced if any single reference point in the physical space fails to map to a point in model space within a specified error threshold. Each potential correlation combination is evaluated by one or more criteria to determine the correlation between segmented markers in model space and physical localization element locations. Examples of evaluation criteria include computing the transformation using three points, and then projecting the remaining physical points to model space as described previously. Other examples include incorporating coil orientation information between the segmented markers and 5- or 6-degrees of freedom (DOF) localization elements, or applying externally available information, such as requiring the user to attach the localization elements in a certain configuration. This correlation technique can account for physical localization elements being in a slightly different relative position than the model space markers since the localization elements process can be performed when the localization elements are anywhere in the periodic cycle of the dynamic body.

After the correlation process, the processor 30 can perform an automatic registration process. The process of registration tracks temporal movement of the dynamic body via the movement of the markers 22, and when temporally valid, computes the transformation between the physical space and the model space.

A measure of a temporal position is referred to herein as a "cost-function." An automatic registration algorithm uses abstract objects so that the cost-function can be defined/determined at runtime. For example, one possible cost function is the average distance between reference points (e.g., positions of localization elements 24). Cost-functions can compute a temporal measure for a group of reference points independent of the space in which the points are known since the measure is based upon landmark positions relative to each other. Once the correlation is established, the localization element locations in physical space can be periodically evaluated using a cost-function to determine when the dynamic body most closely matches the point in the periodic phase of the first time interval (image acquisition). Examples of cost-functions can include: average distance between markers; max/min axis ratio of bounding ellipsoid; and a ratio between minimum and maximum 3D distance between markers. The cost-function can be, for example, determined in patient model space to ensure that moving the patient and/or localizing machinery will not affect the outcome/solution/computation.

A cost-function can be used to establish a measure of the marker positions within the plurality of images during the first time interval. The same cost-function can then be applied continuously to the correlated localization element positions during the second time interval. When the cost-function indicates that the positions of the localization elements in the second time interval have the same relative positions as the marker positions in the first time interval, then the dynamic body can be identified as being at the same temporal point along the path of motion as the first time interval. During the time that the cost-function indicates that the dynamic body is at the same temporal point along the path of motion as the first time interval, then the automatically correlated markers from the first time interval and localization elements from the second time interval can be used to automatically compute a registration. When the cost-function indicates that the registration is valid, then the position and navigational path of a medical instrument can be displayed on a computer screen superimposed onto images of the dynamic body acquired during the first time interval.

After performing the automated segmentation and correlation processes, a list of position data for the localization elements 24 in image space is obtained. This represents the position of the markers 22, and therefore the position of the dynamic body B when the image dataset was acquired. This information is used as the "temporal reference" for the image dataset and represents the nominal reference point position for the dataset. For multiple images acquired at different points in the patient temporal cycle (e.g., at inspiration and expiration of the respiratory cycle), the segmentation-correlation process can be repeated and a temporal reference position can be determined for each image.

Once the temporal reference is established for each image dataset, a registration filter can be used to compare the position of the localization elements 24 in the physical space to the temporal reference location for each image dataset. If the positions of the localization elements 24 are sufficiently close to the temporal reference for a dataset (i.e., the image dataset), then the dataset can be used for navigation for that temporal moment by computing the affine transformation between the physical space and model space. The transformation is then used to project information such as reformatted images, segmentations, informatics, etc. The threshold that determines how close the physical configuration must be to the locations in the image dataset can be modified at runtime to allow the sensitivity or temporal resolution to be modified.

Through the automatic registration process, the relative marker positions at the time of the 3-D scan can be determined. This acquisition of relative marker position allows the point in the respiratory cycle at which the scan was acquired to be determined and navigation gated to that same point in the cycle during a subsequent medical procedure. The resulting registration is relative to the markers affixed to the patient, which allows the patient to be repositioned relative to the scan gantry, table position, and/or localization machinery without invalidating the registration, as long as the markers remain in a fixed position relative to the patient.

As stated previously, the automatic segmentation-correlation-registration process can be performed using an apparatus that includes a garment, such as a garment disclosed in the '028 application. Such an apparatus can be used with the systems and methods described herein to perform the same automatic-segmentation-registration processes described above, except in such an embodiment, the markers and localization elements are coupled to the patient through the use of a garment. All other devices described with reference to FIGS. 1 and 2 can be used in this embodiment to perform the same automatic segmentation-correlation-registration processes as described above.

Figure 3:
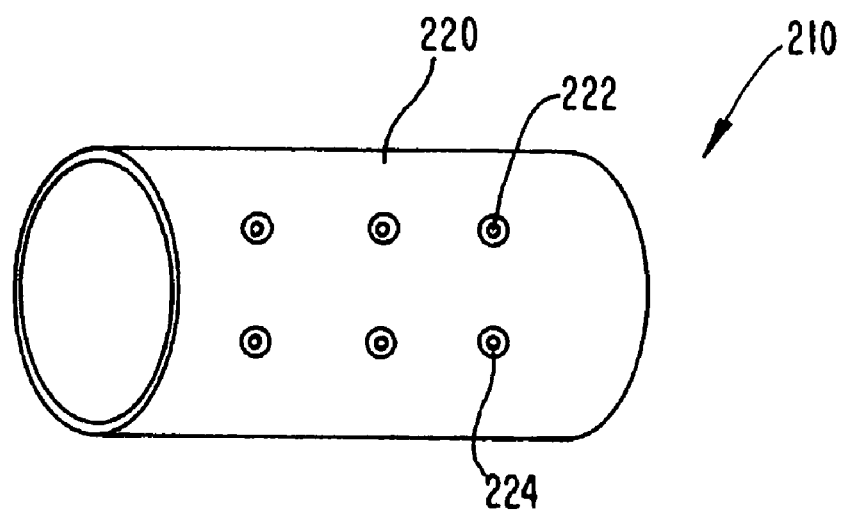
FIG. 3 is a front perspective view of an apparatus according to an embodiment of the invention.

FIG. 3 illustrates an apparatus 210 that includes a garment 220 that is tubular shaped and can be constructed with a flexible and/or stretchable material. This particular garment configuration is only one example of a garment that can be used. It should be understood that other garment configurations can alternatively be used, such as those described in the '028 application. The apparatus 210 further includes multiple markers or fiducials 222 coupled to the garment 220 at spaced locations. A plurality of localization elements 224 are removably coupled proximate to the locations of markers 222, such that during a first time interval as described above, images can be taken without the elements 224 being coupled to the garment 220. In other embodiments, the localization elements 224 need not be removably coupled to the markers 222. For example, the localization elements 224 can be fixedly coupled to the garment 220. In addition, the localization elements 224 can be coupled to the garment 220 during the pre-procedure imaging.

The garment 220 can be positioned over a portion of a patient's body (proximate dynamic anatomy), such as around the upper or lower torso of the patient at a fixed location relative to the patient during both a first time period, in which images are taken of the dynamic anatomy (model or image space), and during a second time period, in which a medical procedure is being performed on the dynamic anatomy (physical space). The stretchability of the garment 220 allows the garment 220 to at least partially constrict some of the movement of the portion of the body for which it is coupled. The markers 222 are coupled to the garment 220 at a fixed location on the garment 220, thus the markers 222 are also coupled to the patient at a fixed location relative to the dynamic anatomy during both the first time period and the second time period.

Figure 4:
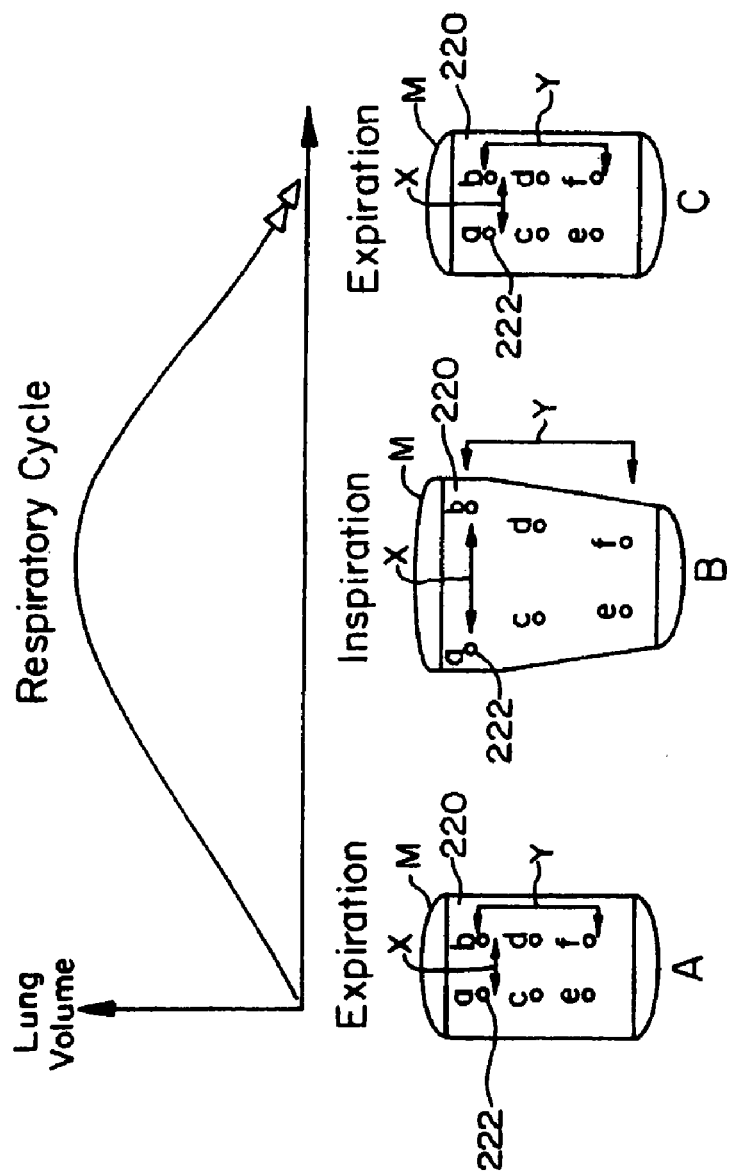
FIG. 4 is a graphical representation illustrating the function of an apparatus according to an embodiment of the invention.

FIG. 4 is a graphical illustration indicating how the apparatus 210 (shown without localization elements 224) can move and change orientation and shape during movement of a dynamic body, such as a mammalian body M. The graph is one example of how the lung volume can change during inhalation (inspiration) and exhalation (expiration) of the mammalian body M. The corresponding changes in shape and orientation of the apparatus 210 during inhalation and exhalation are also illustrated. Although FIG. 4 is being described with reference to an embodiment including a garment, an embodiment that does not include a garment can be similarly described. The six markers 222 shown in FIG. 3 are labeled a, b, c, d, e, and f. As described above, images of the dynamic anatomy with the apparatus 210 coupled thereto can be taken during a first time interval. The images can include an indication of relative position of each of the markers 222, that is the markers 222 are visible in the images, and the position of each marker 222 can then be identified over a period of time. As illustrated, during expiration of the mammalian body M at times indicated as A and C, a distance X between markers a and b is smaller than during inspiration of the mammalian body M, at the time indicated as B. Likewise, a distance Y between markers b and f is greater during inspiration than during expiration.

Figure 7:
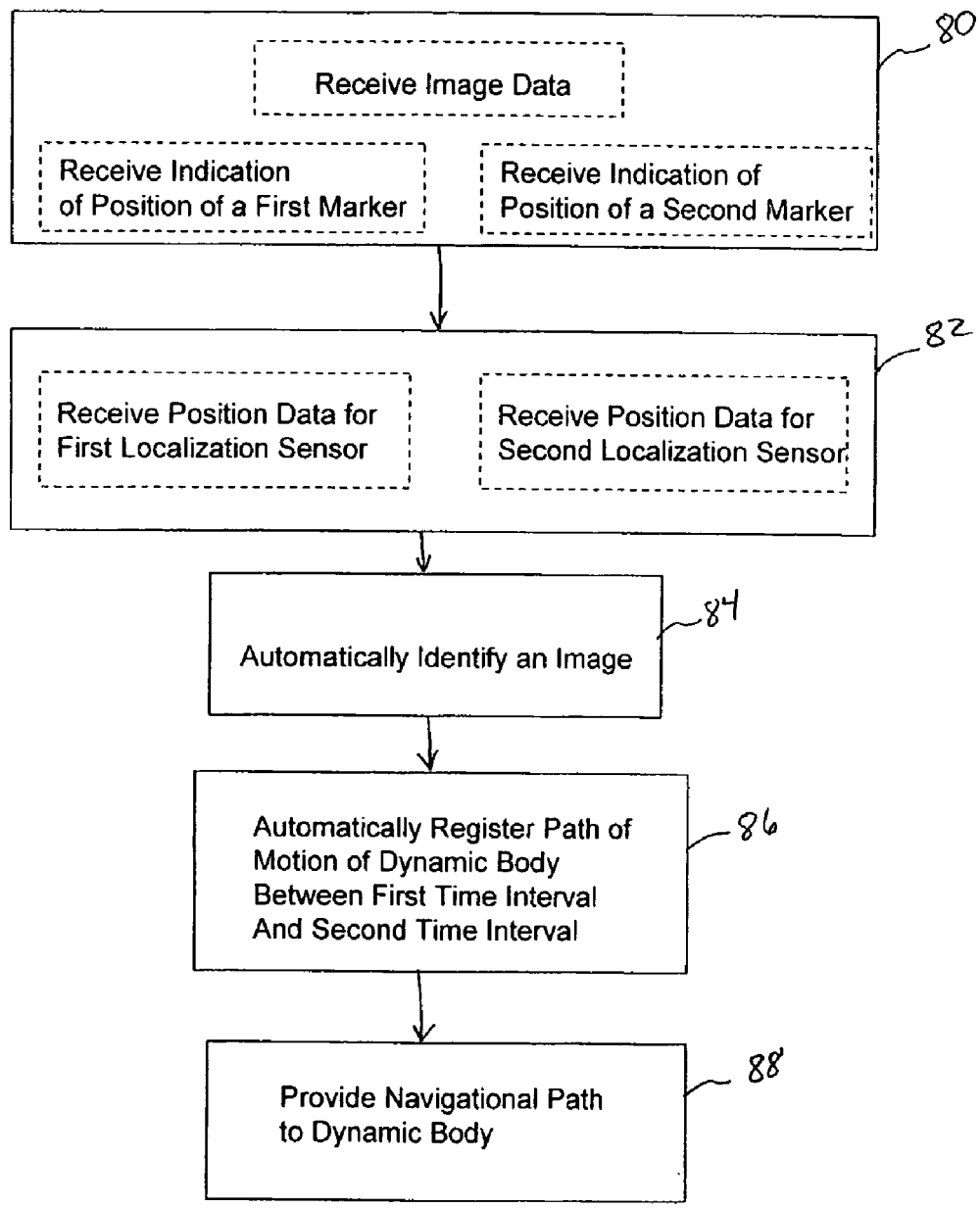
FIG. 7 is a flowchart illustrating a method according to an embodiment of the invention.

FIG. 7 is a flowchart illustrating a method according to another embodiment of the invention. A method includes at step 80 receiving during a first time interval image data associated with a plurality of images of a dynamic body. The plurality of images include an indication of a position of a first marker on a garment coupled to the dynamic body and a position of a second marker on the garment coupled to the dynamic body. The first marker is coupled to the garment at a first location and the second marker is coupled to the garment at a second location. The first time interval is associated with a path of motion of the dynamic body. At step 82, data associated with a position of a first localization element relative to the dynamic body is received, and data associated with a position of a second localization element relative to the dynamic body is received during a second time interval after the first time interval. The first localization element is coupled to the garment at the first location, and the second localization element is coupled to the garment at the second location. The second time interval is associated with a path of motion of the dynamic body and the garment is coupled to the dynamic body in a fixed position relative to the dynamic body during both the first time interval and the second time interval.

During the second time interval, an image from the plurality of images associated with a position of the first marker that is substantially the same as the position of the first localization element relative to the dynamic body and a position of the second marker that is substantially the same as the position of the second localization element relative to the dynamic body are automatically identified at step 84. The automatic identification can be based on an appearance of the markers within the identified image. The automatic identification can also include identifying a position of a third localization element, and projecting that position on to the image data set and determining whether a third marker exists in an image from the image data set at the position of the third localization element. The automatic identification can also include correlating a position of the first localization element during the second time interval with the position of the first marker in the plurality of images. At step 86, the path of motion of the dynamic body is automatically registered during the second time interval is automatically registered with the path of motion of the dynamic body during the first time interval. The automatic registering in step 86 can include identifying at least one temporal reference within the plurality of images and identifying whether the at least one temporal reference is associated with at least one of the first marker or the second marker providing a navigational path for a medical instrument to be directed based on the identified image.

At step 88, a navigational path is provided for a medical instrument to be directed based on the identified image. A physician can use the navigational path to guide a medical instrument to the dynamic body while performing a medical procedure on the dynamic body during the second time interval.

CONCLUSION

While various embodiments of the invention have been described above, it should be understood that they have been presented by way of example only, and not limitation. Thus, the breadth and scope of the invention should not be limited by any of the above-described embodiments, but should be defined only in accordance with the following claims and their equivalents.

The previous description of the embodiments is provided to enable any person skilled in the art to make or use the invention. While the invention has been particularly shown and described with reference to embodiments thereof, it will be understood by those skilled in art that various changes in form and details may be made therein without departing from the spirit and scope of the invention. For example, the garment, markers and localization elements can be constructed from any suitable material, and can be a variety of different shapes and sizes, not necessarily specifically illustrated, while still remaining within the scope of the invention.

While a relatively small number of markers are discussed, the system is scalable and the use of any number of markers is contemplated. For example, a garment may include between 2 and 20 markers, 10-50 markers, etc. Additionally, variations in the automated processes can be used to achieve the same, or substantially the same, desired results.

What is claimed is:

1. A non-transitory processor-readable medium storing code representing instructions to cause a processor to perform a process, the code comprising code to:
   receive, during a first time interval, image data associated with a plurality of 3-D images of a dynamic body during a path of motion of the dynamic body, the 3-D images taken using an imaging device, the dynamic body having an apparatus coupled to the dynamic body, the apparatus having a plurality of radiopaque markers physically coupled thereto, wherein the plurality of radiopaque markers change in orientation relative to each other during the first time interval, and wherein the plurality of radiopaque markers are visible in the 3-D images and the images provide an indication of a position in a model space of each of the plurality of radiopaque markers;
   receive, during a second time interval after the first time interval, data associated with a plurality of localization elements physically coupled to the apparatus proximate the plurality of radiopaque markers, the data sent to the processor from the plurality of localization elements and including a position in a physical space of each of the plurality of localization elements during a path of motion of the dynamic body, wherein the plurality of localization elements change in orientation relative to each other during the second time interval;
   automatically compare the data associated with the position of each of the localization elements from the plurality of localization elements with the position of each radiopaque marker from the plurality of radiopaque markers identified from the data associated with a plurality of 3-D images; and
   automatically identifying a first radiopaque marker from the plurality of radiopaque markers within the plurality of 3-D images having substantially the same position as a first localization element from the plurality of localization elements relative to the dynamic body based on the comparing.

2. The non-transitory processor-readable medium of claim 1, further comprising code to: select an image from the plurality of images associated with the identified radiopaque marker.

3. The non-transitory processor-readable medium of claim 1, further comprising code to:
automatically identify a second radiopaque marker from the plurality of radiopaque markers within the plurality of 3-D images having substantially the same position as a second localization element from the plurality of localization elements relative to the dynamic body based on the comparing; and
select an image from the plurality of 3-D images associated with the identified first radiopaque marker and the identified second radiopaque marker.

4. The non-transitory processor-readable medium of claim 1, further comprising code to:
receive during the second time interval data associated with a position in the physical space of a third localization element relative to the dynamic body, the third localization element coupled to the dynamic body;
project the position of the third localization element from the physical space to the data associated with a plurality of images in the model space; and
determine that a third radiopaque marker either one of exists or does not exists in an image from the plurality of images at substantially the same position as the third localization element.

5. The non-transitory processor-readable medium of claim 1, wherein the automatically identifying includes automatically correlating the identified position of the localization element with a position of the radiopaque marker within an image from the plurality of images.

6. The non-transitory processor-readable medium of claim 3, further comprising code to:
automatically register the path of motion of the dynamic body associated with the second time interval with the path of motion of the dynamic body associated with the first time interval, based on the automatically identifying.

7. A non-transitory processor-readable medium storing code representing instructions to cause a processor to perform a process, the code comprising code to:
receive, during a first time interval, image data associated with a plurality of 3-D images of a dynamic body during a path of motion of the dynamic body, the 3-D images taken using an imaging device, the dynamic body having an apparatus coupled thereto, the apparatus having a plurality of radiopaque markers physically coupled thereto, wherein the plurality of radiopaque markers change in orientation relative to each other during the first time interval, and wherein the plurality of radiopaque markers are visible in the 3-D images;
receive, during a second time interval after the first time interval, data associated with a plurality of localization elements physically coupled to the apparatus proximate the plurality of radiopaque markers, the data sent to the processor from the plurality of localization elements and including a position in a physical space of each of the plurality of localization elements during a path of motion of the dynamic body, wherein the plurality of localization elements change in orientation relative to each other during the second time interval;
automatically segment the data associated with the plurality of 3-D images from the first time interval to identify a position in a model space of each of the at least one radiopaque markers from the plurality of radiopaque markers;
automatically correlate the data associated with the position of the at least one radiopaque markers from the plurality of radiopaque markers from the first time interval with the data associated with the position of each of the localization elements from the plurality of localization elements from the second time interval; and
automatically register a path of motion of the dynamic body during the first time interval with a path of motion of the dynamic body during the second time interval based on the automatically correlating.

8. The non-transitory processor-readable medium of claim 6, wherein the automatic registration includes identifying at least one temporal reference within the plurality of images and whether the at least one temporal reference is associated with at least one of the first radiopaque marker or the second radiopaque marker, wherein the identifying provides a navigational path for a medical instrument to be directed based on the identified image.

9. The non-transitory processor-readable medium of claim 8, wherein the navigational path is used to guide a medical instrument to the dynamic body while performing a medical procedure on the dynamic body during the second time interval.

10. The non-transitory processor-readable medium of claim 7, further comprising code to:
automatically identify a first radiopaque marker and a second radiopaque marker from the plurality of radiopaque markers within the plurality of 3-D images having substantially the same position as a second localization element from the plurality of localization elements relative to the dynamic body based on the comparing; and
identify an image from the plurality of 3-D images associated with the identified first radiopaque marker and the identified second radiopaque marker.

11. The non-transitory processor-readable medium of claim 10, wherein the automatic registration includes identifying at least one temporal reference within the plurality of images and whether the at least one temporal reference is associated with at least one of the first radiopaque marker or the second radiopaque marker, wherein the identifying provides a navigational path for a medical instrument to be directed based on the identified image.

12. The non-transitory processor-readable medium of claim 11, wherein the navigational path is used to guide a medical instrument to the dynamic body while performing a medical procedure on the dynamic body during the second time interval.

* * * * *